(12) United States Patent
Huepf et al.

(10) Patent No.: US 12,290,409 B2
(45) Date of Patent: May 6, 2025

(54) METHOD AND SYSTEMS FOR INCREASING TRANSMIT POWER DURING AN ULTRASOUND SCAN

(71) Applicant: General Electric Company, Schenectady, NY (US)

(72) Inventors: Thomas Huepf, Schoefling a.A. (AT); Christian Fritz Perrey, Mondsee (AT); Thomas Andrew Kraus, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 707 days.

(21) Appl. No.: 16/237,154

(22) Filed: Dec. 31, 2018

(65) Prior Publication Data

US 2020/0205787 A1 Jul. 2, 2020

(51) Int. Cl.
A61B 8/00 (2006.01)

(52) U.S. Cl.
CPC .............. *A61B 8/56* (2013.01); *A61B 8/4483* (2013.01); *A61B 8/463* (2013.01); *A61B 8/546* (2013.01)

(58) Field of Classification Search
CPC ......... A61B 8/56; A61B 8/4483; A61B 8/463; A61B 8/546
See application file for complete search history.

(56) References Cited

U.S. PATENT DOCUMENTS

| | | | |
|---|---|---|---|
| 6,210,335 B1 | 4/2001 | Miller | |
| 6,436,045 B1* | 8/2002 | Rafter | A61B 8/467 600/447 |
| 6,824,518 B2 | 11/2004 | Von Behren et al. | |
| 8,267,867 B2* | 9/2012 | Abe | A61B 8/4455 600/459 |
| 2004/0102703 A1* | 5/2004 | Behren | G01S 7/52098 600/443 |
| 2010/0016719 A1 | 1/2010 | Freiburger et al. | |
| 2013/0345563 A1* | 12/2013 | Stuebe | A61B 5/316 600/440 |
| 2014/0018708 A1* | 1/2014 | Dunbar | A61B 34/25 601/2 |
| 2016/0228091 A1* | 8/2016 | Chiang | A61B 8/0883 |

(Continued)

FOREIGN PATENT DOCUMENTS

CN 105796128 A 7/2016

OTHER PUBLICATIONS

Bigelow, Timothy A. et al., "The Thermal Index: Its Strengths, Weaknesses and Proposed Improvements", 2011, Journal of Ultrasound in Medicine 2011, vol. 30, No. 5, pp. 714-734 (Year: 2011).*

(Continued)

*Primary Examiner* — John D Li
(74) *Attorney, Agent, or Firm* — McCoy Russell LLP (57) ABSTRACT

Various methods and systems are provided for ultrasound imaging. In one embodiment, a method comprises, during an ultrasound scan, acquiring a series of ultrasound frames with a first transmit power, receiving a command to pause the ultrasound scan, and acquiring at least one ultrasound frame with a second transmit power higher than the first transmit power responsive to receiving the command. In this way, the image quality of an image displayed while a scan is paused may be increased.

19 Claims, 6 Drawing Sheets

(56) References Cited

U.S. PATENT DOCUMENTS

2016/0338591 A1* 11/2016 Lachenbruch ......... G16H 20/40
2017/0053396 A1* 2/2017 Zhai ..................... A61B 8/5207

OTHER PUBLICATIONS

Harris, Gerald R. et al., "Comparison of Thermal Safety Practice Guidelines for Diagnostic Ultrasound Exposure", 2016, Ultrasound in Med. & Biol., vol. 42, No. 2, pp. 345-357 (Year: 2016).*
State Intellectual Property Office of the People's Republic of China, Office Action and Search Report Issued in Application No. 201911315608.2, Aug. 16, 2022, 27 pages. (Submitted with Partial Translation).

* cited by examiner

METHOD AND SYSTEMS FOR INCREASING TRANSMIT POWER DURING AN ULTRASOUND SCAN

FIELD

Embodiments of the subject matter disclosed herein relate to ultrasound imaging.

BACKGROUND

Medical diagnostic ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Such transducer elements of the ultrasound probe typically include electromechanical elements capable of converting electrical energy into mechanical energy for transmission of ultrasonic waves into patient tissue and mechanical energy back into electrical energy when the reflected ultrasonic waves reach the transducers.

BRIEF DESCRIPTION

In one embodiment, a method comprises, during an ultrasound scan, acquiring a series of ultrasound frames with a first transmit power, receiving a command to pause the ultrasound scan, and acquiring a limited number of 'prepause' ultrasound frames with a second transmit power. In this way, the image quality of a freeze frame displayed while a scan is paused may be increased.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
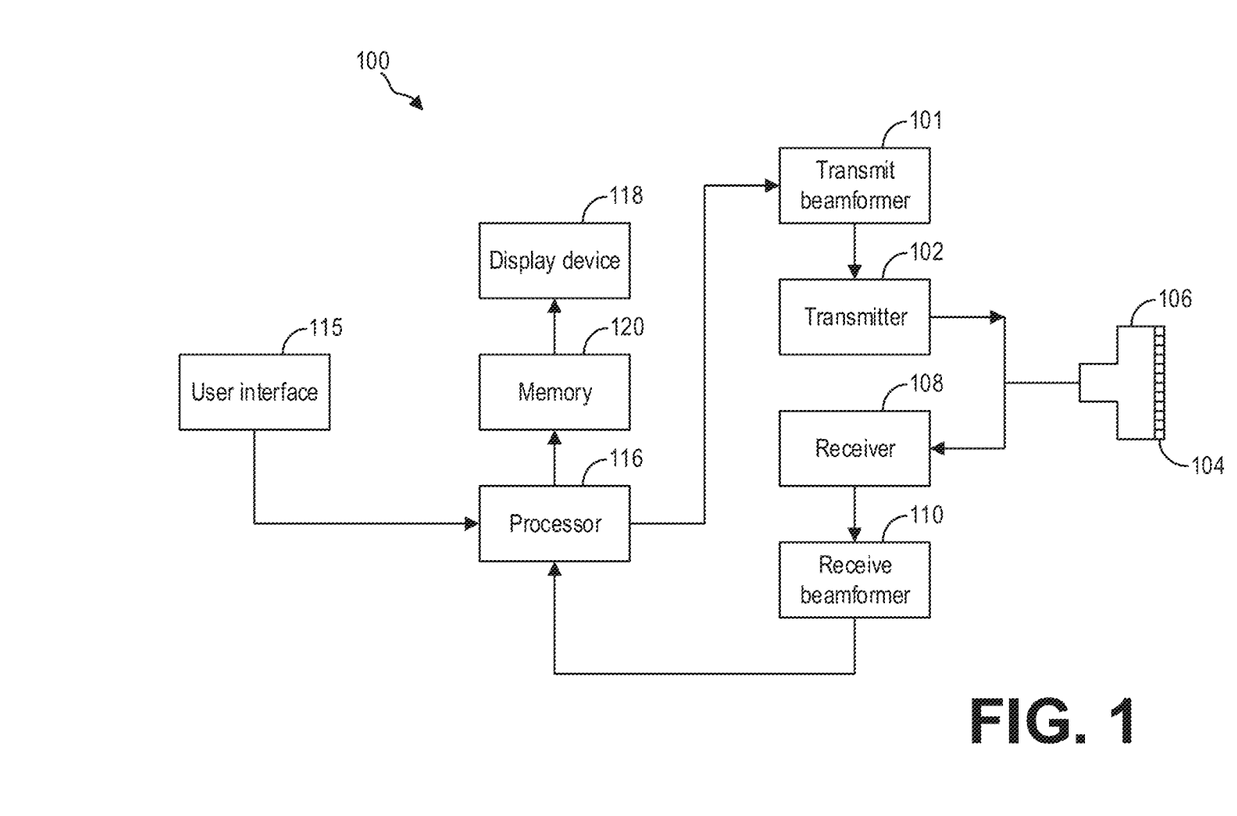
FIG. 1 shows an example ultrasound imaging system according to an embodiment.

The following description relates to various embodiments of ultrasound imaging, such as the ultrasound imaging system shown in FIG. 1. In particular, systems and methods for increasing transmit power during an ultrasound scan are provided. One of the many factors for determining image quality is the acoustic transmit power. With higher transmit power, a better signal-to-noise ratio (SNR) is achieved and in turn a higher image quality is obtained. However, transmit power is constrained by several safety parameters, such as mechanical index and thermal index. Mechanical index is an ultrasound safety parameter that estimates the maximum negative amplitude of the pressure pulse in tissue and indicates the likelihood of bioeffects such as cavitation that may cause tissue damage. Regulatory agencies such as the United States Food and Drug Administration (FDA) establish ultrasound regulations that set an upper limit on mechanical index for diagnostic applications. Thermal index is an ultrasound safety parameter that estimates the thermal bioeffects of an ultrasound beam, as the absorption of sound waves may cause heating in tissue. To that end, the thermal index comprises a ratio of acoustic power at the depth of interest to the estimated power necessary to raise the tissue equilibrium temperature by one degree Celsius. Another thermal limit is the rate of change in tissue temperature dT comprising a measure of the rate at which tissue temperature changes. The thermal limits depend on a measure of time-averaged acoustic power and thus depends on the duration of exposure. For example, the temperature rise of tissue depends on the number of pulses transmitted in a given period of time—with more pauses between the pulses, less temperature rise will occur. This leads to a tradeoff between pulse repetition frequency and energy per pulse. Since the thermal index typically assumes a long duration of exposure, a method for ultrasound imaging, such as the method depicted in FIG. 2, includes increasing the transmit power for a series of last frames in a transmit sequence responsive to an operator of the ultrasound imaging system pausing the ultrasound scan. As depicted in FIG. 3, the transmit power may be increased above thermal limits for the last frames in the transmit sequence prior to a pause in the transmit sequence. In turn, the image quality of the freeze frame or the image displayed during the pause may be correspondingly higher than the image quality of ultrasound frames or images displayed during a continuous acquisition. Similarly, another method for ultrasound imaging, such as the method depicted in FIGS. 4 and 5, includes acquiring multiple frames with a higher transmit power before pausing a scan, and generating a cine sequence from the multiple frames. In addition to increasing the image quality, the penetration depth of ultrasound frames acquired with increased transmit power is also increased, as depicted in FIG. 6.

FIG. 1 is a schematic diagram of an ultrasound imaging system 100 in accordance with an embodiment of the invention. The ultrasound imaging system 100 includes a transmit beamformer 101 and a transmitter 102 that drive elements 104 within a transducer array, or probe, 106 to emit pulsed ultrasonic signals into a body (not shown). According to an embodiment, the transducer array 106 may be a one-dimensional transducer array probe. However, in some embodiments, the transducer array 106 may be a two-dimensional matrix transducer array probe. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system.

A user interface 115 may be used to control operation of the ultrasound imaging system 100, including, to control the input of patient data, to change a scanning or display parameter, and the like. The user interface 115 may include one or more of the following: a rotary, a mouse, a keyboard, a trackball, hard keys linked to specific actions, soft keys that may be configured to control different functions, and a graphical user interface displayed on the display device 118.

The ultrasound imaging system 100 also includes a processor 116 to control the transmit beamformer 101, the transmitter 102, the receiver 108, and the receive beamformer 110. The processer 116 is in electronic communication with the probe 106. For purposes of this disclosure, the term "electronic communication" may be defined to include both wired and wireless communications. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30 Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. A memory 120 is included for storing processed volumes of acquired data. In an exemplary embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. The image lines and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed.

Figure 2:
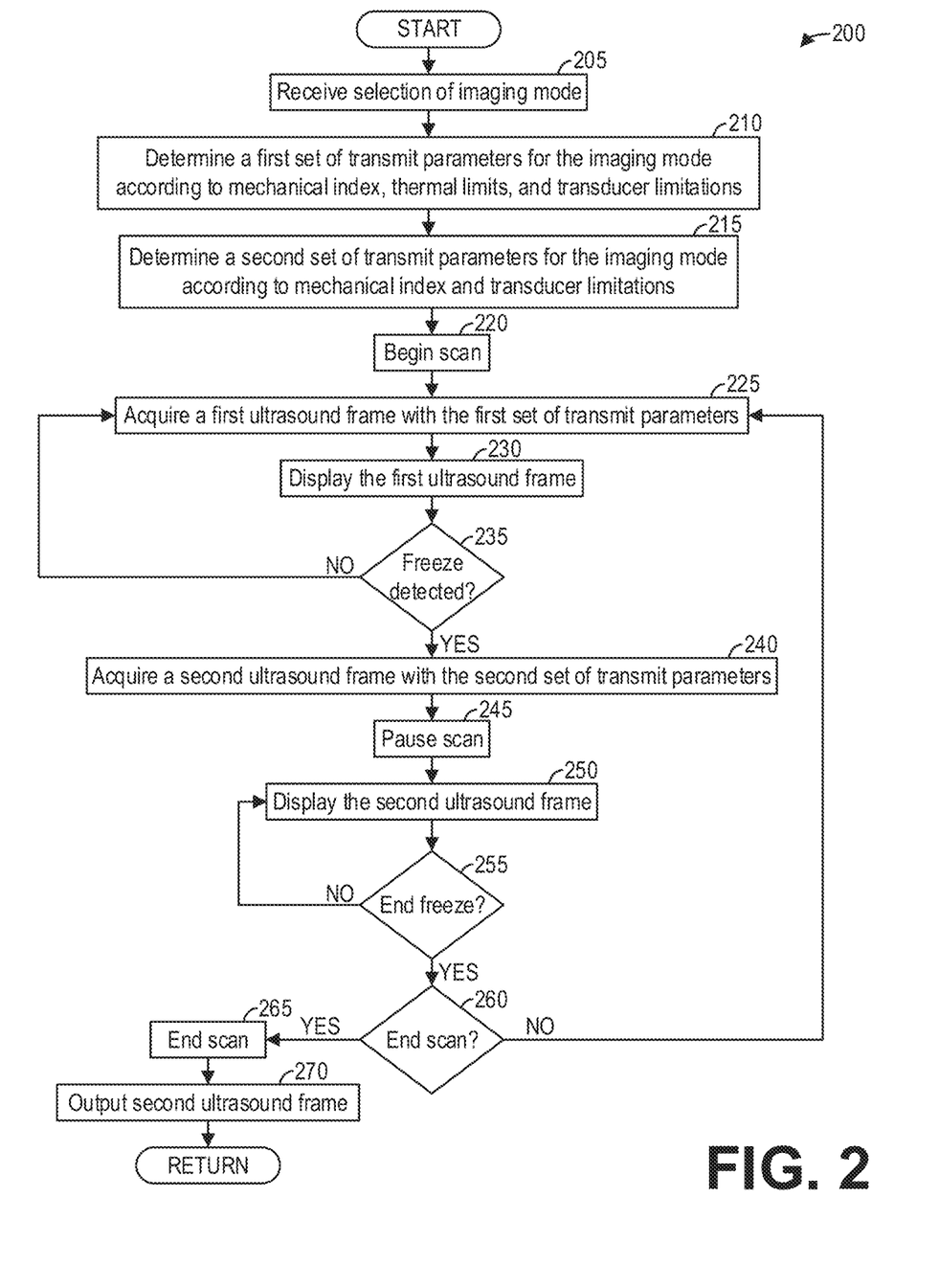
FIG. 2 shows a high-level flow chart illustrating an example method for generating a freeze frame according to an embodiment.
Figure 3:
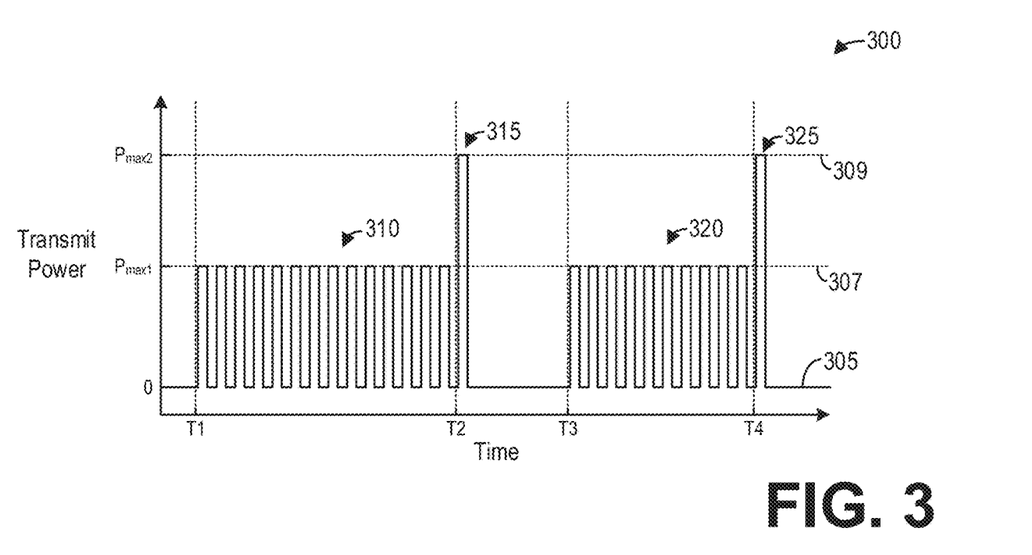
FIG. 3 shows a graph illustrating an example transmit sequence for generating a freeze frame according to an embodiment.

FIG. 2 shows a high-level flow chart illustrating an example method 200 for generating a freeze frame according to an embodiment. In particular, method 200 relates to increasing the transmit power of an ultrasound probe above a thermal limit for a single frame responsive to a user pausing a scan. Method 200 is described with regard to the systems and components of FIG. 1, though it should be appreciated that method 200 may be implemented with other systems and components without departing from the scope of the present disclosure. For example, method 200 may be stored as executable instructions in non-transitory memory, such as memory 120, and may be executed by a processor, such as processor 116, of the ultrasound imaging system 100.

Method 200 begins at 205. At 205, method 200 receives a selection of an imaging mode. The imaging mode may comprise, as illustrative and non-limiting examples, an A-mode, a B-mode, a Doppler mode, an M-mode, a harmonic imaging mode, and so on, including specific types of imaging modes (e.g., a color Doppler mode, a continuous wave Doppler mode, a pulsed wave Doppler mode). The selection of the imaging mode may be input, for example, by an operator of the ultrasound imaging system via the user interface 115. The selection of the imaging mode may further include specified settings relating to the imaging mode and input by the operator. Method 200 thus receives the selection of the imaging mode from the operator.

Continuing at 210, method 200 determines a first set of transmit parameters for the imaging mode according to limitations set by the mechanical index, thermal limits such as the thermal index and the rate of change in tissue temperature dT, and limitations of the ultrasound transducer or probe. The limitations of the ultrasound transducer may include, for example, maximum voltages applicable to transducer elements as well as transducer surface temperature. The limitations set by the mechanical index and the thermal limits as well as transducer surface temperature may be determined from look-up tables that include limits for the given imaging mode. Such limits may be predetermined using phantoms, for example. The limitations may limit, for example, transmit parameters relating to transmit power such as transmit voltage, pulse repetition frequency, number of cycles of a transmit waveform, and line density or spatial distribution of acoustic energy. Thus, method 200 may determine, from the look-up tables for example, a first set of transmit parameters that maximizes transmit power and thus SNR within the limitations set by the mechanical index, the thermal limits, and the transducer limitations.

Continuing at 215, method 200 determines a second set of transmit parameters for the imaging mode according to limitations set by mechanical index as well as limitations of the ultrasound transducer. That is, method 200 determines a second set of transmit parameters that are limited according to the mechanical index and transducer limitations but are not limited by the thermal limits. As both the thermal index, the rate of change in tissue temperature dT, and the transducer surface temperature limitations are typically predetermined by measuring steady-state values after continuously operating an ultrasound imaging system for a sustained duration (e.g., for thirty minutes), method 200 may determine the second set of parameters without regard for the thermal limits such as the thermal index and rate of change in tissue temperature dT as well as the transducer surface temperature limitation. Method 200 thus selects the second set of transmit parameters to maximize the transmit power within the limits of at least the mechanical index.

In some examples, method 200 may determine the second set of transmit parameters according to the limitations of the thermal limits. However, as the second set of transmit parameters will not be used by method 200 for more than a single frame or at most several consecutive frames at the end of a transmit sequence with a duration following thereafter wherein no frames are generated, the rate of change in tissue temperature dT may be ignored. As such, the thermal index may not be the most limiting factor with regard to constraining the transmit parameters.

After determining the second set of transmit parameters, method 200 continues to 220. At 220, method 200 begins the scan. To that end, at 225, method 200 acquires a first ultrasound frame with the first set of transmit parameters. Acquiring the first ultrasound frame comprises transmitting one or more pulses according to the selected imaging mode with the first set of transmit parameters. For example, method 200 transmits ultrasonic pulses via the ultrasound probe 106 by commanding the transmit beamformer 101 and/or transmitter 102 to transmit control signals to the ultrasound transducers 104 of the ultrasound probe 106 according to a pulse sequence for the imaging mode. Acquiring the first ultrasound frame further comprises receiving echoes corresponding to the one or more transmitted pulses. That is, the ultrasonic pulses are reflected within the subject and the reflected waves or echoes are received by the transducer elements 104 of the ultrasound probe 106 and passed to the receiver 108 and receive beamformer 110. Acquiring the first ultrasound frame further comprises processing the received echoes to generate an image or the first ultrasound frame. Continuing at 230, method 200 displays the first ultrasound frame. The first ultrasound frame may be displayed, for example, in real-time via the display device 218.

At 235, method 200 determines whether a Freeze command is detected. A Freeze command may be input by the operator, for example, via the user interface 115, and received by the processor 116 from the user interface 115. Additionally or alternatively, in examples wherein the display device 118 comprises a touch-sensitive display device or a touchscreen, the display device 118 may display a virtual button indicating "Freeze" thereon, and in such examples the operator may issue a Freeze command by pressing the virtual button on the display device 118. It should be appreciated that while the term "Freeze" is used herein to refer to the command to freeze a scan, other terms such as "Pause," "Hold," and other terms indicating a temporary stop of the scan.

If a Freeze command is not detected ("NO"), method 200 returns to 225 to continue scanning and acquiring ultrasound frames with the first set of transmit parameters. Thus, method 200 may continuously scan the patient to acquire ultrasound frames or images for display at 240 during a "Run" mode or "Live" imaging mode.

Then, if a Freeze command is detected at 235 ("YES"), method 200 continues to 240. At 240, method 200 acquires a second ultrasound frame with the second set of transmit parameters. To acquire the second ultrasound frame with the second set of transmit parameters, method 200 transmits one or more ultrasonic pulses via the transducer elements 104 of the transducer probe 106 into the subject. The one or more ultrasonic pulses are transmitted according to the selected imaging mode and the second set of transmit parameters. Acquiring the second ultrasound frame further comprises receiving echoes of the transmitted ultrasonic pulses. That is, the one or more ultrasonic pulses are reflected within the subject and the reflected waves or echoes are received by the transducer elements 104 of the ultrasound probe 106 and passed to the receiver 108 and receive beamformer 110. Acquiring the second ultrasound frame further comprises processing the received echoes to generate an image or the second ultrasound frame. In some examples, the processing of the received echoes may be modified with respect to the processing of echoes at 225 according to the second set of transmit parameters. For example, in addition to determining the first and second sets of transmit parameters at 210 and 215, method 200 may further determine corresponding first and second sets of receive parameters and/or image processing parameters. When acquiring the second ultrasound frame at 240, method 200 may therefore receive and process the echoes to generate the second ultrasound frame according to a second set of receive and/or image processing parameters.

Further, although method 200 is described with regard to acquiring a single ultrasound frame at 240 with the second transmit parameters, it should be appreciated that in some examples, at 240 method 200 may acquire several ultrasound frames with the second set of transmit parameters after the request to freeze or pause the scan is detected at 235. Method 200 acquires at least one second ultrasound frame with the second set of parameters.

As the one or more ultrasonic pulses are transmitted according to the second set of transmit parameters, the second ultrasound frame is therefore acquired with a transmit power that is not limited by thermal limits such as the thermal index and/or the rate of change of tissue temperature dT. The image quality of the second ultrasound frame acquired with the second set of transmit parameters is therefore higher than the image quality of the first ultrasound frame acquired with the first set of transmit parameters.

After acquiring the second ultrasound frame at 240, method 200 continues to 245. At 245, method 200 pauses the scan. Ultrasound frames are not acquired while the scan is paused or frozen. Continuing at 250, method 200 displays the second ultrasound frame via the display device 218. As the second set of transmit parameters provides for an increased acoustic power during the acquisition of the echoes for the second ultrasound frame, the signal-to-noise ratio (SNR) and thus the image quality of the second ultrasound frame is increased relative to the SNR and the image quality of the first ultrasound frame. Furthermore, the penetration depth of the second ultrasound frame may be increased relative to the penetration depth of the first ultrasound frame. The image quality in the far-field (e.g. the bottom of the ultrasound image) in the second ultrasound frame is thereby improved relative to the first ultrasound frame. Thus, the second ultrasound frame comprises a freeze frame which is continuously displayed to the operator while the ultrasound imaging system 100 is in a "Freeze" mode, also referred to herein simply as Freeze.

Further, it should be appreciated that the difference in image quality between the second ultrasound frame and the first ultrasound frame may be so substantial that the second ultrasound frame may look substantially different from the first ultrasound frame when displayed to the operator via the display device 118. Therefore, in some examples, the second ultrasound frame may be blended with the previous first ultrasound frame to improve the consistency between frames while still including increased penetration depth and improved image quality.

Continuing at 255, method 200 determines whether a command to end the Freeze is detected. To command the Freeze to end, the operator may input, for example via the user interface 115 and/or the display device 118, a command to end the Freeze and resume scanning or to end the scan altogether. If a command to end the Freeze is not detected ("NO"), method 200 returns to 250 to maintain the Freeze and continue displaying the second ultrasound frame.

However, if a command to end the Freeze is detected ("YES"), method 200 continues to 260. At 260, method 200 determines if the command to end the Freeze comprises a command to end the scan. If the command to end the Freeze is not a command to end the scan ("NO"), method 200 returns to 225 to resume the scan with the first set of transmit parameters.

However, referring again to 260, if the command to end the Freeze is a command to end the scan ("YES"), method 200 continues to 265. At 265, method 200 ends the scan. At 270, method 200 outputs the second ultrasound frame. For example, method 200 may output the second ultrasound frame to memory, such as memory 120, for storage, and may additionally or alternatively output the second ultrasound frame to a printer, a remote storage device, and so on. Method 200 then returns.

Thus, a method for ultrasound imaging includes increasing the transmit power above a thermal limit for a last frame or image during an ultrasound scan. The thermal index may be overridden for a single frame because the thermal index is determined for a substantially longer duration and therefore the increased power of the ultrasonic frame may not increase the tissue temperature.

As an illustrative example of the method 200 of FIG. 2, FIG. 3 shows a graph 300 illustrating an example transmit sequence 305 for generating a freeze frame according to the method 200 of FIG. 2. In particular, the graph 300 depicts the transmit power as a function of time for the transmit sequence 305. The graph 300 includes a first maximum transmit power 307 determined according to the thermal index and/or rate of change in tissue temperature dT as discussed hereinabove, as well as a second maximum transmit power 309 determined according to the mechanical index instead of the thermal index or rate of change in tissue temperature dT. As depicted, for a given imaging mode, the second maximum transmit power 309 is greater than the first maximum transmit power 307.

As depicted, the ultrasound scan begins at time T1. The transmit sequence 305 thus includes a first set of frames 310 which are limited by the first maximum transmit power 307. Thus, after the time T1, the ultrasound imaging system thus transmits one or more ultrasonic pulses and generates an ultrasound frame from corresponding echoes for each frame in the first set of frames 310. Each frame of the first set of frames 310 is therefore acquired according to a first set of transmit parameters which are constrained by the first maximum transmit power 307.

At time T2, the operator commands the ultrasound imaging system to Freeze or pause the scan. Responsive to detecting the command to Freeze, the ultrasound imaging system acquires a freeze frame 315 with a transmit power limited by the second maximum transmit power 309. To acquire the freeze frame 315, the ultrasound imaging system transmits one or more ultrasonic pulses constrained by the second maximum transmit power 309 and generates the freeze frame 315 from the corresponding echoes. The freeze frame 315 is continuously displayed after the time T2 to the operator of the ultrasound imaging system.

The operator commands the ultrasound imaging system to resume the scan at the time T3. Therefore, after the time T3, the transmit sequence 305 includes a second set of frames 320 limited by the first maximum transmit power. The ultrasound imaging system thus transmits ultrasonic pulses for each frame of the second set of frames 320 and generates the frames from the corresponding echoes after the time T3. At time T4, the operator commands the ultrasound imaging system to freeze and/or end the scan. The transmit sequence 305 thus includes a final freeze frame 325 acquired with the second maximum transmit power 309 after the time T4 before ending the scan. The final freeze frame 325 may then be displayed to the operator at the conclusion of the scan.

Figure 4:
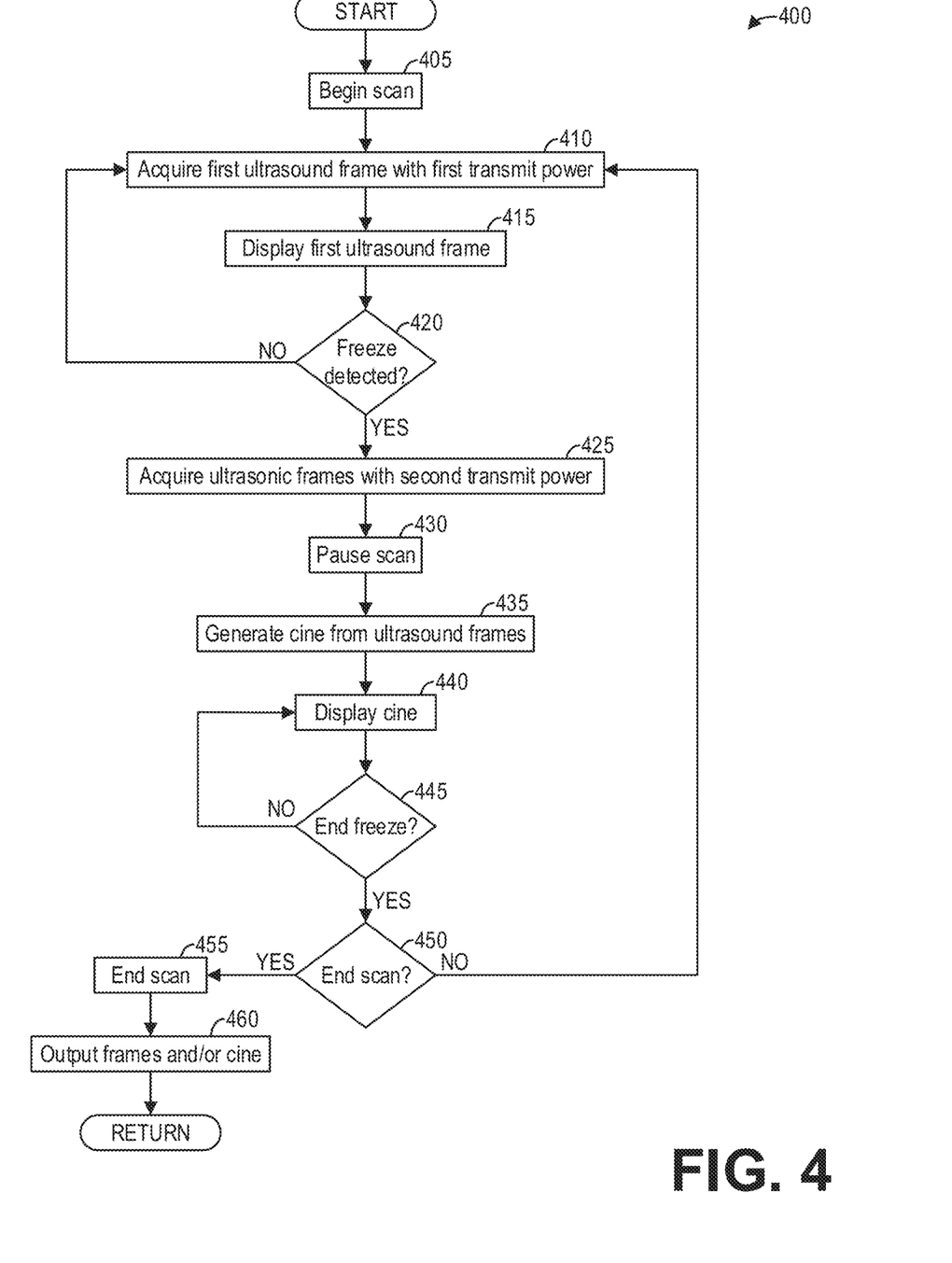
FIG. 4 shows a high-level flow chart illustrating an example method for generating a cine according to an embodiment.

In some examples, more than one frame may be generated after detecting a Freeze command. Multiple freeze images may therefore be acquired after the system is commanded to freeze. In some examples, these multiple freeze images may be combined into a cine or short film which loops on the display, or may be evaluated frame-by-frame by the operator. As an illustrative example, FIG. 4 shows a high-level flow chart illustrating an example method 400 for generating a cine according to an embodiment. In particular, method 400 relates to increasing transmit power for several frames responsive to a command to freeze or pause an ultrasound scan. Method 400 is described with regard to the systems and components of FIG. 1, though it should be appreciated that the method 400 may be implemented with other systems and components without departing from the scope of the present disclosure. For example, method 400 may be stored as executable instructions in non-transitory memory, such as memory 120, and executed by a processor, such as processor 116, of the ultrasound imaging system 100.

Method 400 begins at 405. At 405, method 400 begins a scan. Similar to method 200, method 400 may begin the scan according to a selected imaging mode. At 410, method 400 acquires a first ultrasound frame with a first transmit power. The first transmit power is determined according to a thermal limit, such as the thermal index and/or the rate of change of tissue temperature dT, as the selected imaging mode may indicate that the scan will continue for a sustained duration wherein temperature limits should be considered. To acquire the first ultrasound frame with the first transmit power, method 400 transmits one or more ultrasonic pulses with the first transmit power and generates the first ultrasound frame from received echoes corresponding to the one or more ultrasonic pulses. At 415, method 400 displays the first ultrasound frame, for example via the display device 118.

At 420, method 400 determines if a command to Freeze is detected. If a command to Freeze is not detected ("NO"), method 400 returns to 410 to continue acquiring ultrasonic frames with the first transmit power. Method 400 may therefore continuously scan the patient with the first transmit power.

However, referring again to 420, if a command to Freeze is detected ("YES"), method 400 continues to 425. At 425, method 400 acquires ultrasonic frames with a second transmit power. The second transmit power is determined according to mechanical limits such as the mechanical index and/or the physical limitations of the ultrasound transducer, for example, rather than thermal limits such as the thermal index and/or the rate of change in tissue temperature dT. Method 400 may acquire a set of consecutive ultrasonic frames with the second transmit power. For example, method 400 may acquire more than one consecutive frame but less than a threshold number of frames with the second transmit power. The threshold number of frames may be determined such that the thermal limits may be overridden for the consecutive number of frames. The threshold number of frames may comprise, for example, three to five frames. To acquire each frame of the ultrasonic frames with the second transmit power, method 400 thus transmits one or more ultrasonic pulses with the second transmit power into the subject, receives echoes of the one or more ultrasonic pulses, and generates the frame from the received echoes.

After acquiring the ultrasound frames with the second transmit power, method 400 continues to 430. At 430, method 400 pauses the scan. Method 400 does not acquire ultrasound frames while the scan is paused. Instead, continuing at 435, method 400 generates a cine from the ultrasound frames acquired at 425. A persistence imaging processing algorithm that includes blending or smoothing the ultrasound frames may be applied to generate the cine. In some examples, the cine may be generated from the ultrasound frames acquired at 425 as well as one or more ultrasound frames acquired at 410. For example, the last two ultrasound frames acquired at 410 prior to the Freeze being commanded may be arranged in sequence with the ultrasound frames acquired at 425, and a persistence algorithm may be applied to the sequence of ultrasound frames to generate the cine.

At 440, method 400 displays the cine via the display device 118. The cine may be continuously looped as well as manipulated by the operator. For example, the operator may pause the cine, or step frame-by-frame through the cine to view each ultrasound frame in the sequence. The operator may therefore review a cinematic sequence of ultrasound frames during a scan while suspending or freezing the transmission of ultrasonic waves into the patient. Further, the acquisition of freeze frames with the second transmit power higher than the first transmit power results in an increased image quality of the ultrasound frames acquired at 425 and thus the cine generated at 435. As discussed hereinabove with regard to FIG. 3, the penetration depth of the ultrasound frames acquired at 425 may also be increased relative to the penetration depth of the ultrasound frame acquired at 410.

Continuing at 445, method 400 determines if a command to end the Freeze is detected. If a command to end the Freeze is not detected ("NO"), method 400 returns to 440 to maintain the freeze and continue displaying the cine. However, if a command to end the Freeze is detected ("YES"), method 400 continues to 450. At 450, method 400 determines if the command to end the Freeze is a command to end the scan. If the command to end the Freeze is not a command to end the scan ("NO"), method 400 returns to 410, whereupon method 400 continues the scan by acquiring ultrasound frames with the first transmit power.

However, referring again to 450, if the command to end the Freeze is a command to end the scan ("YES"), method 400 continues to 455. At 455, method 400 ends the scan. At 460, method 400 outputs the ultrasound frames and/or the cine, for example, to memory 120 for subsequent retrieval and review. Method 400 then returns.

Figure 5:
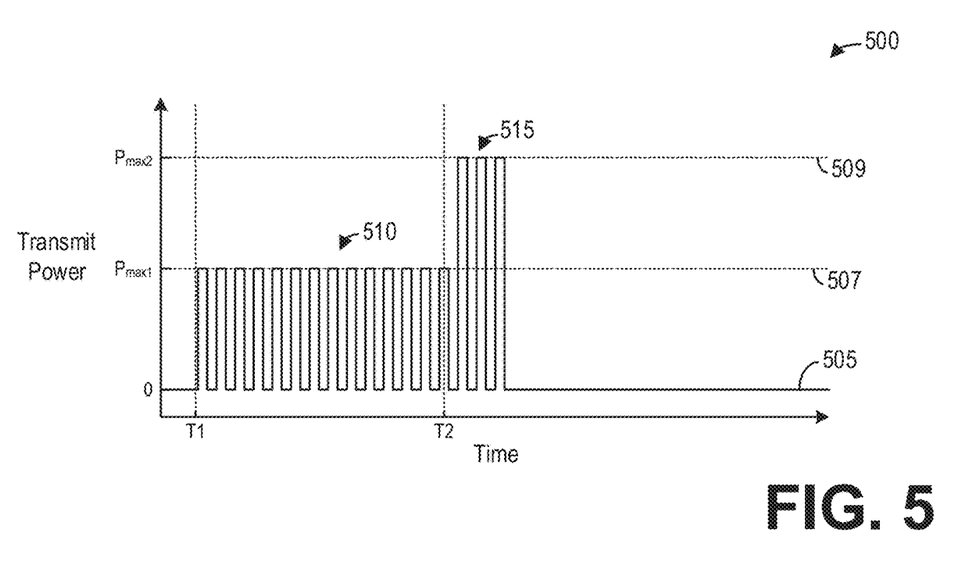
FIG. 5 shows a graph illustrating an example transmit sequence for generating a cine according to an embodiment.
Figure 6:
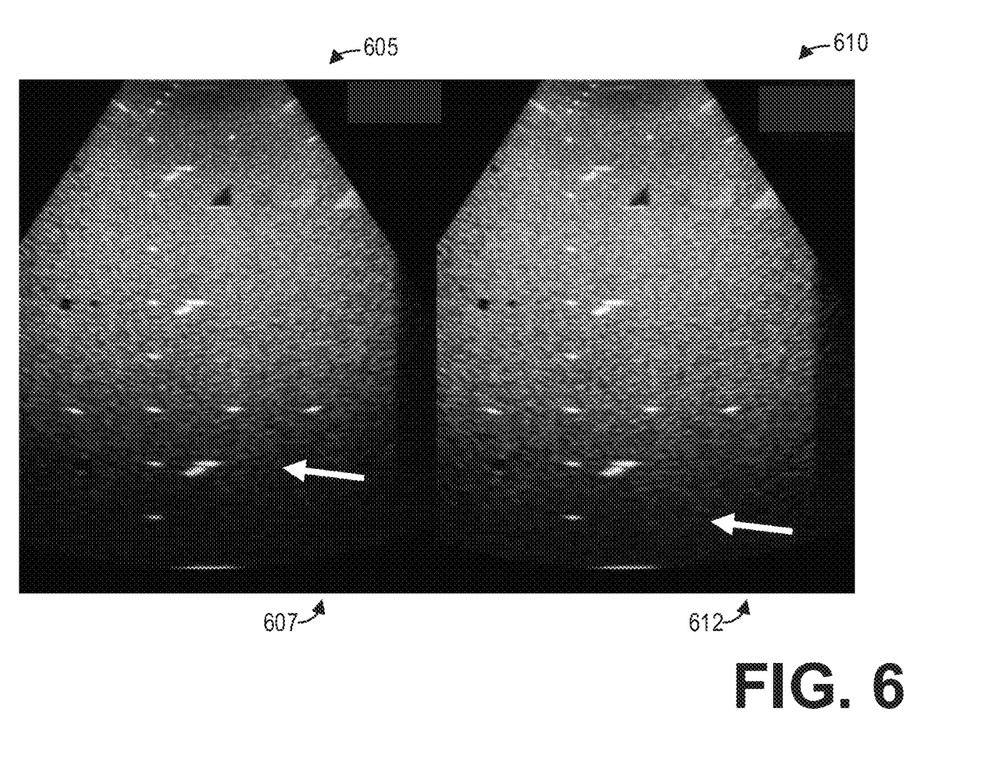
FIG. 6 shows example ultrasound frames according to an embodiment.

As an illustrative example of the method of FIG. 4, FIG. 5 shows a graph 500 illustrating an example transmit sequence 505 for generating a cine according to the method of FIG. 4. Similar to the graph 300 of FIG. 3, the graph 500 depicts the transmit power of ultrasound frames acquired during a scan as a function of time. The graph 500 depicts a first maximum transmit power 507 determined according to a thermal limit such as thermal index and/or the rate of change in tissue temperature dT, as well as a second maximum transmit power 509 determined according to a mechanical limit such as mechanical index. As depicted, the second maximum transmit power 509 is greater than the first maximum transmit power 507. The scan begins at the time T1, and so the transmit sequence 505 includes a first set of frames 510 beginning at the time T1. The first set of frames 510 are limited by the first maximum transmit power 507. At the time T2, the operator commands the ultrasound imaging system to end the scan. As depicted, the command to end the scan is input during the acquisition of the final frame in the first set of frames 510. Rather than disrupting the acquisition of the final frame in the first set of frames 510, the acquisition of the final frame is completed. Further, in response to the command to end the scan, the transmit sequence 505 includes a set of freeze frames 515 that are acquired after the time T2. Each freeze frame of the set of freeze frames 515 is acquired with the second maximum transmit power 509. As depicted, the transmit sequence 505 ends after the acquisition of the set of freeze frames 515. Each freeze frame of the set of freeze frames 515 may be combined to generate a cine, which may be played back in a loop on the display device 118 for review by the operator. In some examples, the cine may be generated from one or more freeze frames of the set of freeze frames 515 as well as one or more of the preceding frames in the first set of frames 510. As an illustrative example, the last two frames of the first set of frames 510 may be combined with the three freeze frames of the set of freeze frames 515 to generate the cine.

FIG. 6 shows example ultrasound frames or images according to an embodiment. In particular, FIG. 6 shows a first ultrasound frame 605 acquired during a scan with a transmit power limited by a thermal limit, as well as a second ultrasound frame 610 acquired during the same scan with a transmit power limited by a mechanical limit. For the first ultrasound frame 605, the rate of change in tissue temperature dT is 8.00 which limits the transmit power. For the second ultrasound frame 610, the acoustic power is increased by approximately 3 dB until the next limiting factor, the mechanical index, is reached. This increase in acoustic power causes the rate of change in tissue temperature dT to increase to 13.9. However, as the second ultrasound frame 610 is acquired at the end of a transmit sequence, the limit of the rate of change in tissue temperature dT can be safely exceeded. Further, in addition to the higher SNR of the second ultrasound frame 610 relative to the SNR of the first ultrasound frame 605, and thus the higher image quality, the penetration depth 607 of the first ultrasound frame 605 (indicated by the white arrow) is increased by several centimeters to the penetration depth 612 of the second ultrasound frame 610 (indicated by the white arrow). The increased acoustic power thus improves the quality of the far-field in the second ultrasound frame 610.

A technical effect of the disclosure includes the increase of transmit power for acquisition of an ultrasound frame above a thermal limit for a limited duration. Another technical effect of the disclosure includes the increased signal-to-noise ratio and image quality of a final ultrasound frame acquired during an ultrasound scan. Yet another technical effect of the disclosure includes the ultrasonic imaging of a patient with a first transmit power for a sustained duration, and the ultrasonic imaging of the patient with a second transmit power higher than the first transmit power for a single frame at the end of the sustained duration.

In one embodiment, a method comprises, during an ultrasound scan, acquiring a series of ultrasound frames with a first transmit power, receiving a command to pause the ultrasound scan, and acquiring at least one ultrasound frame with a second transmit power higher than the first transmit power responsive to receiving the command.

In a first example of the method, the first transmit power is constrained by a thermal limit, and the second transmit power is constrained by a mechanical limit. In a second example of the method optionally including the first example, the second transmit power exceeds the thermal limit. In a third example of the method optionally including one or more of the first and second examples, acquiring the series of ultrasound frames with the first transmit power comprises, for each ultrasound frame of the series of ultrasound frames, transmitting one or more ultrasonic pulses according to a first set of transmit parameters limited by the thermal limit including one or more of a first transmit voltage, a first pulse repetition frequency, and a first spatial distribution of acoustic energy. In a fourth example of the method optionally including one or more of the first through third examples, acquiring the at least one ultrasound frame with the second transmit power comprises transmitting one or more ultrasonic pulses according to a second set of transmit parameters limited by the mechanical limit including one or more of a second transmit voltage and a second spatial distribution of acoustic energy. In a fifth example of the method optionally including one or more of the first through fourth examples, the thermal limit comprises one or more of a thermal index and a rate of change in tissue temperature, and the mechanical limit comprises a mechanical index. In a sixth example of the method optionally including one or more of the first through fifth examples, the method further comprises receiving echoes for the at least one ultrasound frame, and pausing transmission of ultrasonic pulses. In a seventh example of the method optionally including one or more of the first through sixth examples, the method further comprises displaying the at least one ultrasound frame while the ultrasound scan is paused. In an eighth example of the method optionally including one or more of the first through seventh examples, the method further comprises receiving a command to resume the ultrasound scan, and acquiring a second series of ultrasound frames with the first transmit power. In a ninth example of the method optionally including one or more of the first through eighth examples, the method further comprises blending the at least one ultrasound frame and at least one ultrasound frame of the series of ultrasound frames into a blended ultrasound frame, and displaying the blended ultrasound frame.

In another embodiment, a method comprises, during an ultrasound scan, acquiring a series of ultrasound frames by transmitting ultrasonic pulses into a subject with a first transmit power limited by a thermal limit, displaying the series of ultrasound frames, receiving a command to pause the ultrasound scan, acquiring a set of ultrasound frames with a second transmit power higher than the first transmit power, pausing the ultrasound scan, and displaying a cine generated from the set of ultrasound frames.

In a first example of the method, the method further comprises generating the cine from the set of ultrasound frames by blending the set of ultrasound frames. In a second example of the method optionally including the first example, the method further comprises generating the cine from at least one ultrasound frame of the series of ultrasound frames by blending the at least one ultrasound frame with the set of ultrasound frames. In a third example of the method optionally including one or more of the first and second examples, the method further comprises receiving a command to resume the ultrasound scan, acquiring a second series of ultrasound frames with the first transmit power, and displaying the second series of ultrasound frames. In a fourth example of the method optionally including one or more of the first through third examples, the thermal limit comprises one of a thermal index and a rate of change of tissue temperature.

In yet another embodiment, a system comprises an ultrasound probe, a user interface configured to receive input from an operator of the system, a display device, and a processor configured with instructions in non-transitory memory that when executed cause the processor to: during an ultrasound scan, control the ultrasound probe to acquire a series of ultrasound frames with a first transmit power; display, via the display device, the series of ultrasound frames; receive, via the user interface, a command to pause the ultrasound scan; control the ultrasound probe to acquire one or more ultrasound frames with a second transmit power higher than the first transmit power; pause the ultrasound scan after acquiring at least one of the one or more ultrasound frames; and display, via the display device, at least one ultrasound frame of the one or more ultrasound frames acquired with the second transmit power while the ultrasound scan is paused.

In a first example of the system, the first transmit power is constrained by a thermal limit of one or more of a subject being scanned and the ultrasound probe. In a second example of the system optionally including the first example, the second transmit power is constrained by a mechanical limit of one or more of the subject and the ultrasound probe. In a third example of the system optionally including one or more of the first and second examples, the processor is further configured with instructions in the non-transitory memory that when executed cause the processor to generate a blended ultrasound frame by blending at least one ultrasound frame of the one or more ultrasound frames with at least one ultrasound frame of the series of ultrasound frames, and display the blended ultrasound frame while the ultrasound scan is paused. In a fourth example of the system optionally including one or more of the first through third examples, the processor is further configured with instructions in the non-transitory memory that when executed cause the processor to receive a command to resume the ultrasound scan, and control the ultrasound probe to acquire a second series of ultrasound frames with the first transmit power.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
receiving a first user command, wherein the first user command is an imaging mode selection;
initiating an ultrasound scan in response to receiving the first user command;
during the ultrasound scan that was initiated in response to the first user command, acquiring a series of ultrasound frames with a first transmit power, wherein the first transmit power is based on a first set of transmit parameters, wherein the first set of transmit parameters constrain the first transmit power based on thermal limits, the thermal limits including a rate of change in tissue temperature;
displaying the series of ultrasound frames acquired with the first transmit power; and
continuing the ultrasound scan and acquiring ultrasound frames with the first transmit power until a second user command is received, wherein the second user command is a command to pause the ultrasound scan, and wherein the command to pause the ultrasound scan is a user command to reduce the transmit power from the first transmit power to no transmit power;
receiving the second user command to pause the ultrasound scan while the ultrasound scan is ongoing with the first transmit power; and
responsive to receiving the second user command to pause the ultrasound scan while the ultrasound scan is ongoing with the first transmit power,
immediately acquiring at least one ultrasound frame with a second transmit power higher than the first transmit power, wherein the second transmit power is based on a second set of transmit parameters that ignores the rate of change in tissue temperature; then
pausing transmission of ultrasonic pulses by reducing the second transmit power to no transmit power until a third user command is received, wherein the third user command is a command to resume the ultrasound scan; then
receiving the third user command while the transmission of ultrasonic pulses is paused;
resuming the scan responsive to the third user command, where resuming the scan includes acquiring a second series of ultrasound frames with the first transmit power;
receiving a fourth user command, wherein the fourth user command is a command to end the ultrasound scan;
responsive to receiving the command to end the ultrasound scan,
acquiring a final freeze frame with the second transmit power higher than the first transmit power responsive to the command to end the ultrasound scan;
outputting the final freeze frame to memory; and
concluding the ultrasound scan and ceasing transmission of ultrasonic pulses for the ultrasound scan after acquiring the final freeze frame,
wherein the ultrasound scan is immediately transitioned from the first transmit power to the second transmit power and then paused every time the second user command is received while the ultrasound scan is ongoing with the first transmit power.

2. The method of claim 1, wherein the thermal limits for the first set of transmit powers further include a thermal index and a transducer surface temperature limitation, and wherein the second transmit power is constrained by a mechanical limit.

3. The method of claim 2, wherein the second transmit power exceeds the thermal limits, and wherein the thermal index estimates thermal bioeffects of an ultrasound beam heating the tissue.

4. The method of claim 2, wherein acquiring the series of ultrasound frames with the first transmit power comprises, for each ultrasound frame of the series of ultrasound frames, transmitting one or more ultrasonic pulses according to the first set of transmit parameters limited by the thermal limits, including a first transmit voltage, a first pulse repetition frequency, and a first spatial distribution of acoustic energy, and wherein the second set of transmit parameters further ignore the thermal index and the transducer surface temperature limitation.

5. The method of claim 4, wherein acquiring the at least one ultrasound frame with the second transmit power comprises transmitting one or more ultrasonic pulses according to the second set of transmit parameters limited by the mechanical limit including one or more of a second transmit voltage and a second spatial distribution of acoustic energy.

6. The method of claim 2, wherein the mechanical limit comprises a mechanical index.

7. The method of claim 2, wherein the ultrasound scan is immediately transitioned from the first transmit power to the second transmit power and then concluded every time the fourth user command is received while the ultrasound scan is ongoing with the first transmit power, and wherein the thermal index comprises a ratio of acoustic power at a depth of interest to an estimated power necessary to raise an equilibrium temperature of the tissue by one degree Celsius.

8. The method of claim 1, wherein the second transmit power is used immediately before pausing the transmission of the ultrasonic pulses, and wherein the second transmit power is not limited by thermal limits.

9. The method of claim 1, further comprising blending the at least one ultrasound frame acquired at the second transmit power and the last two ultrasound frames of the series of ultrasound frames acquired at the first transmit power prior to receiving the second user command to pause the ultrasound scan to generate a cine, and displaying the cine, and wherein the last two ultrasound frames acquired at the first transmit power and the at least one ultrasound frame acquired at the second transmit power are arranged in sequence for generating the cine.

10. A method, comprising:

receiving a first user command, wherein the first user command is an imaging mode selection;

initiating an ultrasound scan in response to receiving the first user command;

during the ultrasound scan that was initiated in response to the first user command, acquiring a series of ultrasound frames by transmitting ultrasonic pulses with a first transmit power limited by thermal limits into a subject, the thermal limits including a rate of change in tissue temperature;

displaying the series of ultrasound frames; and continuing the ultrasound scan and acquiring ultrasound frames with the first transmit power until a second user command is received, wherein the second user command is a command to pause the ultrasound scan, and wherein the command to pause the ultrasound scan is an indication to temporarily stop the ultrasound scan;

receiving the second user command to pause the ultrasound scan while the ultrasound scan is ongoing with the first transmit power;

responsive to receiving the second user command to pause the ultrasound scan while the ultrasound scan is ongoing with the first transmit power, immediately transitioning from acquiring ultrasound frames with the first transmit power to acquire a set of ultrasound frames by transmitting further ultrasonic pulses with a second transmit power, wherein the second transmit power is higher than the first transmit power, and wherein acquiring the set of ultrasonic frame includes overriding the rate of change in tissue temperature and ignoring the rate of change in tissue temperature while acquiring the set of ultrasound frames; then pausing the ultrasound scan; and displaying a cine generated from the set of ultrasound frames, the cine comprising a video loop, receiving a third user command to end the ultrasound scan while the ultrasound scan is paused;

responsive to receiving the third user command to end the ultrasound scan while the ultrasound scan is paused, outputting the cine to memory; and ending the ultrasound scan, wherein pausing the ultrasound scan includes pausing the ultrasonic pulses and pausing the further ultrasonic pulses, and wherein the ultrasound scan is immediately transitioned from the first transmit power to the second transmit power and then paused every time the second user command is received while the ultrasound scan is ongoing with the first transmit power.

11. The method of claim 10, further comprising generating the cine from the set of ultrasound frames by blending the set of ultrasound frames.

12. The method of claim 11, wherein the cine is generated only from the set of ultrasound frames acquired at the second transmit power after receiving the second user command and prior to pausing the ultrasound scan.

13. The method of claim 10, further comprising receiving the command to resume the ultrasound scan, acquiring a second series of ultrasound frames with the first transmit power, and displaying the second series of ultrasound frames.

14. The method of claim 10, wherein the thermal limits comprise both a thermal index and the rate of change of tissue temperature, wherein the second transmit power is used immediately before pausing the ultrasound scan, and wherein the second transmit power is not limited by the thermal index and the rate of change of the tissue temperature thermal limits.

15. A system, comprising:

an ultrasound probe;

a user interface configured to receive input from an operator of the system;

a display device; and a processor configured with instructions in non-transitory memory that when executed cause the processor to:

receive a first user command, wherein the first user command is an imaging mode selection;

initiate an ultrasound scan in response to receiving the first user command;

during the ultrasound scan that was initiated in response to the first user command, transmit ultrasonic pulses via the ultrasound probe and control the ultrasound probe to acquire a series of ultrasound frames with a first transmit power, wherein the first transmit power is constrained by thermal limits, the thermal limits including a thermal index, a rate of change in tissue temperature, and a transducer surface temperature limitation;

display, via the display device, the series of ultrasound frames; and continue the ultrasound scan and acquiring ultrasound frames with the first transmit power until a second user command is received via the user interface, wherein the second user command is a command to pause the ultrasound scan;

receive the second user command to pause the ultrasound scan while the ultrasound scan is ongoing with the first transmit power;

control the ultrasound probe to acquire one or more ultrasound frames with a second transmit power higher than the first transmit power responsive to the command to pause the ultrasound scan, wherein the second transmit power is not constrained by the thermal limits including the thermal index, the rate of change in tissue temperature, and the transducer surface temperature limitation; then pause the ultrasound scan after acquiring at least one ultrasound frame of the one or more ultrasound frames until a third user command is received via the user interface, where pausing the ultrasound scan includes pausing the transmission of ultrasonic pulses via the ultrasound probe;

display, via the display device, an ultrasound freeze frame of the one or more ultrasound frames acquired with the second transmit power while the ultrasound scan is paused;

resume transmitting ultrasonic pulses via the ultrasound probe responsive to receiving the third user command via the user interface while the ultrasound scan is paused, wherein the third user command is either a command to resume the ultrasound scan or to initiate a second scan; and end the ultrasound scan responsive to receiving a fourth user command while the ultrasound scan is paused, wherein the ultrasound freeze frame is saved to memory responsive to receiving the fourth user command to end the ultrasound scan while the ultrasound scan is paused, and wherein the ultrasound scan is immediately transitioned from the first transmit power to the second transmit power and then paused every time the second user command is received while the ultrasound scan is ongoing with the first transmit power.

16. The system of claim 15, wherein the second transmit power is used immediately before pausing the ultrasound scan.

17. The system of claim 16, wherein the second transmit power is constrained by a mechanical limit of one or more of the subject and the ultrasound probe, wherein acquiring the one or more ultrasound frames with the second transmit power includes increasing acoustic power from the first transmit power that is constrained by the thermal limits until the mechanical limit is reached, wherein the mechanical limit is based on a mechanical index, and wherein the mechanical index estimates a maximum negative amplitude of a pressure pulse in tissue.

18. The system of claim 15, wherein the processor is further configured with instructions in the non-transitory memory that when executed cause the processor to generate a blended ultrasound frame for the ultrasound freeze frame by blending at least one ultrasound frame of the one or more ultrasound frames with at least one ultrasound frame of the series of ultrasound frames, and display the blended ultrasound frame while the ultrasound scan is paused.

19. The system of claim 15, wherein the processor is further configured with instructions in the non-transitory memory that when executed cause the processor to control the ultrasound probe to acquire a second series of ultrasound frames with the first transmit power responsive to receiving the command to resume the ultrasound scan.

* * * * *